(12) United States Patent
Kremer et al.

(10) Patent No.: US 11,071,843 B2
(45) Date of Patent: Jul. 27, 2021

(54) DYNAMIC MASKING DEPENDING ON SOURCE OF SNORING

(71) Applicant: BOSE CORPORATION, Framingham, MA (US)

(72) Inventors: Kathleen Elizabeth Kremer, Southborough, MA (US); Jeffrey M. Ellenbogen, Towson, MD (US); Matthew Chace Carpenter, North Attleboro, MA (US); Steven Carl Pletcher, Hopkinton, MA (US); Chia-Ling Li, Framingham, MA (US)

(73) Assignee: BOSE CORPORATION, Framingham, MA (US)

( * ) Notice: Subject to any disclaimer, the term of this patent is extended or adjusted under 35 U.S.C. 154(b) by 292 days.

(21) Appl. No.: 16/278,373

(22) Filed: Feb. 18, 2019

(65) Prior Publication Data

US 2020/0261687 A1    Aug. 20, 2020

(51) Int. Cl.
*A61M 21/02* (2006.01)
*A61B 5/08* (2006.01)
(Continued)

(52) U.S. Cl.
CPC ............. *A61M 21/02* (2013.01); *A61B 5/024* (2013.01); *A61B 5/0816* (2013.01); *A61B 5/24* (2021.01);
(Continued)

(58) Field of Classification Search
CPC .......... A61M 2205/3561; A61M 21/02; A61M 2021/0088; A61M 2021/0027;
(Continued)

(56) References Cited

U.S. PATENT DOCUMENTS

| 5,444,786 A | 8/1995 | Raviv |
| 9,191,744 B2 | 11/2015 | Anderson |

(Continued)

FOREIGN PATENT DOCUMENTS

| EP | 1 886 707 A1 | 2/2008 |
| WO | 2020086169 A2 | 4/2020 |

OTHER PUBLICATIONS

International Search Report and Written Opinion for International Application No. PCT/US2020/018337 dated Jun. 9, 2020, 12 pp.

(Continued)

*Primary Examiner* — Navin Natnithithadha
*Assistant Examiner* — Sunita Reddy
(74) *Attorney, Agent, or Firm* — Patterson + Sheridan, LLP

(57) ABSTRACT

Aspects of the present disclosure provide methods, apparatuses, and systems for dynamically masking audible breathing noises determined to be generated by one or more sleeping partners. According to aspects, a subject's sleep is protected by detecting audible breathing noises in a sleeping environment, determining the audible breathing noises are not generated by the subject, and mitigating the perception of the audible breathing noises that are determined to originate from another subject, such as a bed partner, pet, etc. The dynamic masking reduces the subject's exposure to unnecessary sounds and reduces the chances of masking sounds disturbing the subject's sleep.

20 Claims, 3 Drawing Sheets

(51) Int. Cl.
*G06F 3/16* (2006.01)
*A61B 5/00* (2006.01)
*H04R 1/40* (2006.01)
*A61B 5/024* (2006.01)
*A61B 5/04* (2006.01)
*A61B 5/24* (2021.01)
*A61B 5/11* (2006.01)
*A61M 21/00* (2006.01)
*H04R 1/04* (2006.01)

(52) U.S. Cl.
CPC .......... *A61B 5/4812* (2013.01); *A61B 5/4815* (2013.01); *G06F 3/165* (2013.01); *H04R 1/406* (2013.01); *A61B 5/0006* (2013.01); *A61B 5/11* (2013.01); *A61B 5/4836* (2013.01); *A61B 2560/0242* (2013.01); *A61M 2021/0027* (2013.01); *A61M 2021/0088* (2013.01); *A61M 2205/3303* (2013.01); *A61M 2205/3561* (2013.01); *A61M 2230/06* (2013.01); *A61M 2230/42* (2013.01); *H04R 1/04* (2013.01); *H04R 2420/07* (2013.01)

(58) Field of Classification Search
CPC ...... A61M 2205/3303; A61M 2230/42; A61M 2230/06; A61B 5/389; A61B 5/024; A61B 5/4812; A61B 2560/0242; A61B 5/0816; A61B 5/398; A61B 5/0205; A61B 5/02405; A61B 5/369; A61B 5/24; A61B 5/4815; A61B 5/11; A61B 5/0006; A61B 5/4806; A61B 5/4836; A61B 5/318; A61B 5/6803; G06F 3/165; H04R 2420/07; H04R 1/04; H04R 1/406; A61L 35/11; G10K 11/178; G10K 11/1752
USPC ..................................................... 600/26-28
See application file for complete search history.

(56) References Cited

U.S. PATENT DOCUMENTS

| | | | |
|---|---|---|---|
| 9,579,060 B1 | 2/2017 | Lisy et al. | |
| 10,791,986 B1* | 10/2020 | Kahn | A61B 5/0002 |
| 2004/0234080 A1* | 11/2004 | Hernandez | G10K 11/1783 |
| | | | 381/71.11 |
| 2007/0173730 A1* | 7/2007 | Bikko | A61B 5/6803 |
| | | | 600/538 |
| 2008/0097764 A1 | 4/2008 | Grill et al. | |
| 2008/0243014 A1 | 10/2008 | Moussavi et al. | |
| 2009/0147965 A1* | 6/2009 | Kuo | G10K 11/002 |
| | | | 381/71.6 |
| 2010/0258123 A1* | 10/2010 | Somaiya | A61M 16/024 |
| | | | 128/204.23 |
| 2010/0283618 A1* | 11/2010 | Wolfe | A61B 7/003 |
| | | | 340/575 |
| 2011/0295083 A1* | 12/2011 | Doelling | A61B 5/11 |
| | | | 600/301 |
| 2014/0051938 A1* | 2/2014 | Goldstein | A61B 5/4818 |
| | | | 600/301 |
| 2015/0194144 A1 | 7/2015 | Park et al. | |
| 2015/0258301 A1* | 9/2015 | Trivedi | A61B 5/6898 |
| | | | 600/28 |
| 2015/0281829 A1 | 10/2015 | Gauger, Jr. et al. | |
| 2015/0294662 A1 | 10/2015 | Ibrahim | |
| 2015/0320588 A1* | 11/2015 | Connor | A61F 7/0085 |
| | | | 607/107 |
| 2016/0015315 A1* | 1/2016 | Auphan | A61B 5/6892 |
| | | | 600/301 |
| 2016/0217672 A1* | 7/2016 | Yoon | A61B 5/02055 |
| 2017/0051551 A1 | 2/2017 | Smart | |
| 2017/0281119 A1 | 10/2017 | Stroman | |
| 2017/0319817 A1* | 11/2017 | Morishima | A61B 5/6824 |
| 2017/0323630 A1 | 11/2017 | Stickney et al. | |
| 2018/0078732 A1 | 3/2018 | Keshavan et al. | |
| 2018/0078733 A1 | 3/2018 | Freed et al. | |
| 2018/0078735 A1 | 3/2018 | Dalgleish et al. | |
| 2018/0082550 A1 | 3/2018 | Read et al. | |
| 2018/0236191 A1* | 8/2018 | Martin | A61M 16/0051 |
| 2019/0029563 A1* | 1/2019 | Seis | A61B 7/003 |
| 2019/0030278 A1* | 1/2019 | Kremer | A61B 5/4812 |
| 2019/0046794 A1 | 2/2019 | Goodall et al. | |
| 2019/0073990 A1 | 3/2019 | Moss et al. | |
| 2019/0099009 A1* | 4/2019 | Connor | A47C 21/048 |
| 2020/0086076 A1 | 3/2020 | Mcelhone et al. | |
| 2020/0160828 A1* | 5/2020 | Taki | H04R 3/005 |

OTHER PUBLICATIONS

International Search Report and Written Opinion for International Application No. PCT/US2020/018479 dated Jun. 16, 2020, 14 pp.
International Search Report and Written Opinion for International Application No. PCT/US2020/018483, dated Jun. 9, 2020. 12 pp.

* cited by examiner

DYNAMIC MASKING DEPENDING ON SOURCE OF SNORING

FIELD

Aspects of the present disclosure generally relate to dynamically protecting sleep. More particularly, aspects dynamically output masking sounds to protect a first subject's sleep in an effort to selectively compensate for the audible breathing noises determined to originate from a second subject.

BACKGROUND

Disruptions to a subject's sleep may result in poor sleep which negatively affects the subject's health. Sleep disruptions may be caused by environmental or ambient noises in the subject's sleeping environment that interrupt the subject's sleep.

To try to block or compensate for such noises, a steady, blanket masking sound may be output in the subject's sleeping environment. However, the blanket masking sound is typically played throughout the entire time period the subject is sleeping at a constant, unchanging volume and frequency. Depending on the varying volumes, frequencies, and changes of the environmental noises and the subject's sleep physiology, the blanket masking sound may be ineffective at compensating for some environmental noises, or may itself disrupt the subject's sleep. Additionally, blanket masking exposes the subject to masking sounds for long periods of time regardless of whether the mask is necessary to protect the subject's sleep. As such, a need exists for intelligently masking sounds in a manner that is tailored to the subject and the subject's sleeping environment.

SUMMARY

All examples and features mentioned herein can be combined in any technically possible manner.

In one aspect, an audio device comprises at least one microphone configured to detect audible breathing noises in a sleeping environment, at least one biosensor configured to monitor a breathing architecture of a first subject, a processing unit configured to compare the audible breathing noises to the breathing architecture of the first subject to determine the detected audible breathing noises originated from a second subject, and at least one speaker configured to output a masking sound to compensate for the detected audible breathing noises.

The processing unit may be further configured to determine, based on the comparison of the audible breathing noises to the breathing architecture of the first subject, that a portion of the audible breathing noises originated from the first subject, and the at least one speaker may be configured to refrain from outputting a masking sound to compensate for the portion of the audible breathing noises determined to originate from the first subject. The processing unit may be further configured to determine a time-frequency pattern of the audible breathing noises originating from the second subject, and the masking sound may be aligned with the determined pattern.

The at least one biosensor may be configured to measure at least one biosignal parameter indicative of a sleep condition of the first subject. The at least one biosignal parameter may comprise at least one of a heart rate, heart rate variability, respiration rate, electroencephalogram (EEG), electrooculogram (EOG), electromyogram (EMG), or motion of the first subject. The processing unit may be further configured to adjust the masking sound based on detected audible breathing noises and the at least one measured biosignal parameter. Adjusting the masking sound may comprise adjusting at least one of: a spectral content of the masking sound, a sound pressure level of the masking sound, or an active noise reduction (ANR) level. Monitoring the breathing architecture of the first subject may comprise measuring at least one of: a breathing pattern of the first subject or vibrations of the first subject.

In another aspect, a method for protecting a sleep pattern of a first subject comprises detecting audible breathing noises in a sleeping environment, monitoring a breathing architecture of the first subject while the first subject is sleeping in the sleeping environment, comparing the audible breathing noises to the breathing architecture of the first subject to identify a portion of the audible breathing noises predicted to disrupt the first subject's sleep, determining a pattern of the portion of the audible breathing noises predicted to disrupt the first subject's sleep, and outputting a masking sound to compensate for the portion of the audible breathing noises predicted to disrupt the first subject's sleep, wherein the masking sound is time aligned with the pattern.

The method may further comprise receiving, from the first subject, at least one of: one or more characteristics of the sleeping environment or one or more characteristics of the breathing architecture of the first subject prior to the comparing. The method may further comprise measuring at least one biosignal parameter of the first subject. One or more values of the biosignal parameter may be indicative of a sleep condition of the first subject prior to the comparing. The at least one biosignal parameter may comprise at least one of a heart rate, heart rate variability, respiration rate, electroencephalogram (EEG), electrooculogram (EOG), electromyogram (EMG), or motion of the first subject.

The comparing may further comprise comparing the audible breathing noises, the breathing architecture of the first subject, and the sleep condition of the first subject to identify the portion of the audible breathing noises predicted to disrupt the first subject's sleep. The method may further comprise adjusting the masking sound prior to outputting the masking sound based on the sleep condition of the first subject and the portion of the audible breathing noises predicted to disrupt the first subject's sleep. Adjusting the masking sound may comprise adjusting at least one of: a spectral content of the masking sound, a sound pressure level of the masking sound, or an active noise reduction (ANR) level. Comparing the audible breathing noises to the breathing architecture of the first subject may further comprise identifying a second portion of the audible breathing noises that are not predicted to disrupt the first subject's sleep, and may further comprise refraining from outputting a masking sound for the identified second portion of the audible breathing noises.

In yet another aspect, an audio system comprises at least one microphone for detecting audible breathing noises in a sleeping environment and at least one biosensor for monitoring a breathing architecture of a first subject and for measuring at least one biosignal parameter of the first subject. One or more values of the biosignal parameter are indicative of a sleep condition of the first subject. The audio system further comprises a processing unit configured to compare the audible breathing noises, the breathing architecture of the first subject, and the sleep condition of the first subject, predict whether the audible breathing noises will disturb the subject's sleep based on the comparison to identify predicted disturbing noises, and determine a pattern of the predicted disturbing noises. The audio system further comprises at least one speaker for outputting a masking sound to compensate for the predicted disturbing noises. The masking sound is time aligned with the pattern of the predicted disturbing noises.

The processing unit may be further configured to determine a second subject is in the sleeping environment. The audio system may further comprise an occupancy sensor configured to determine presence of the second subject in the sleeping environment. The processing unit may be further configured to receive input from the first subject regarding characteristics of breathing architecture of the first subject and how many subjects are in the sleeping environment.

A first device may comprise the at least one biosensor, and wherein the first device is a wearable device. The first device may further comprise the at least one speaker. A second device may comprise the at least one microphone, and wherein the second device is a bedside unit. The second device may further comprises the at least one speaker.

Advantages of dynamically masking based on determining breathing noises originated from a source other than the subject will be apparent from the description and the claims.

DETAILED DESCRIPTION

Figure 1:
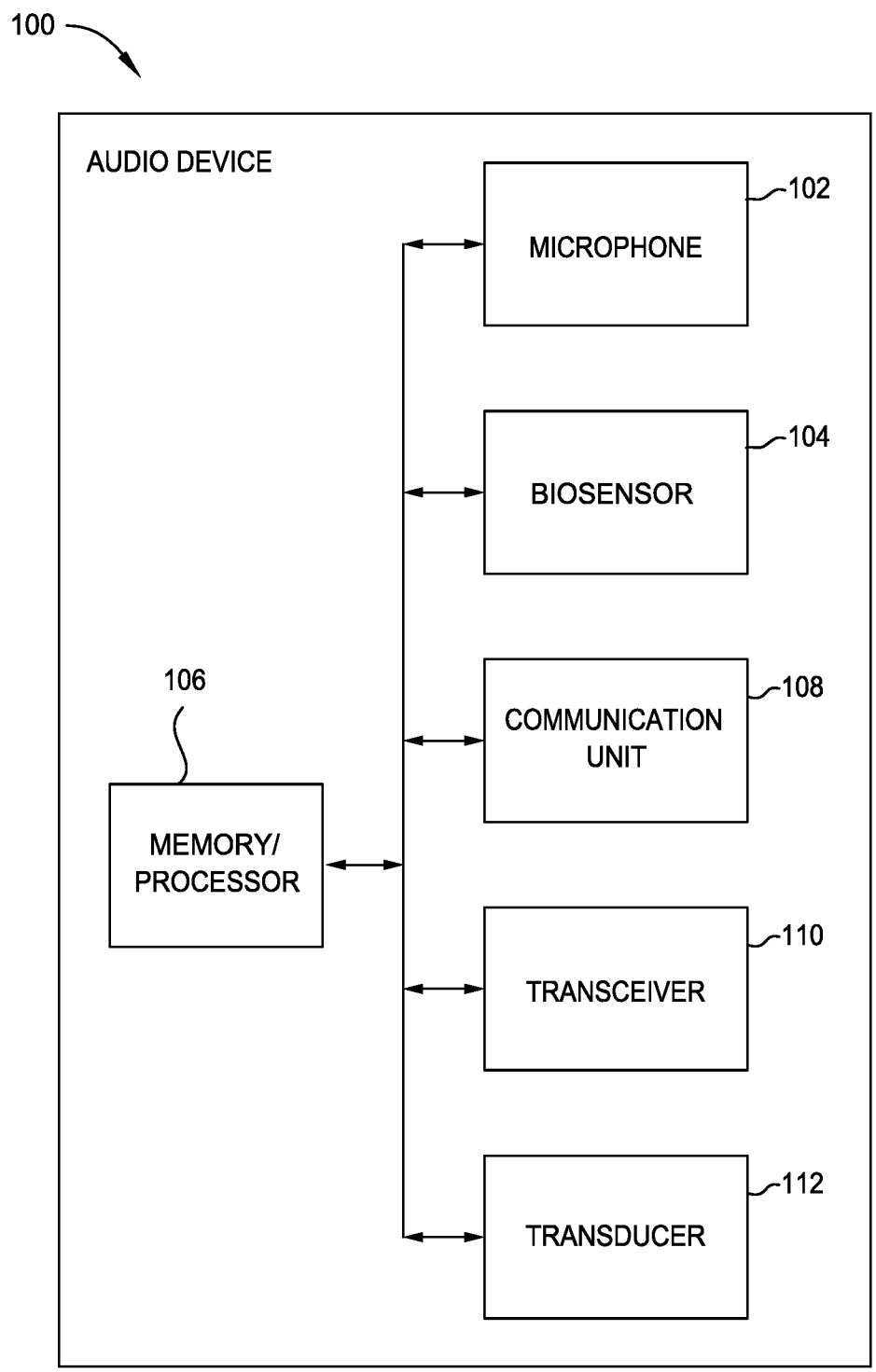
FIG. 1 illustrates example components of an audio device.

A subject's probability of sleep disruption is based, at least in part, on a condition of the subject's sleep. A condition of sleep refers to, for example, how deeply the subject is sleeping. As used herein, sleep condition may refer to sleep physiology, sleep fragility, sleep vulnerability, or other terms referring to the likelihood of a subject's sleep being disrupted.

In one example, the condition of sleep is associated with sleep stages. Stage N3 sleep is the deepest type of non-rapid eye movement (NREM) sleep. Stage N2 sleep is lighter and more fragile than stage N3 sleep. For a same sound intensity, a subject has an increased likelihood of sleep disruption when in stage N2 sleep than when in stage N3 sleep.

A sleep assistance device that outputs masking sounds attempts to protect a subject's sleep. Static masking sounds such as shaped noise or soundscapes may help subjects fall and stay asleep; however, subjects may not enjoy continuously listening to sound while falling asleep and subjects may be exposed to more acoustic energy than necessary to mask noise and protect sleep Exposing subjects to masking noise throughout a duration of a subject's sleep may cause undesirable effects. For example, the masking sounds may disrupt the subject's sleep when the masking sounds are unnecessary or too loud based on one or more of the ambient noise and the subject's sleep condition. Even if the subject's sleep is not disrupted, the subject may be exposed to masking sounds at a higher level than necessary to protect sleep, thereby increasing potential acoustic trauma to the subject's auditory system.

While the term "masking sound" is used throughout, the described methods, apparatuses, and systems are not limited to outputting and adjusting only masking sounds. The term "masking sound" as used herein includes other such sounds to be played in a sleeping environment, such as soothing sounds, audio therapeutics, relaxation soundtracks, entrainment soundtracks, etc.

As used herein, audible breathing noises refer to snoring or sounds during inhalation or exhalation. In aspects, audible breathing noises refer to sounds that occur primarily during inhalation. A person's sleep is generally not disturbed by the noise of his own breathing; however, audible breathing noises from another person or other living subject(s) often disturb a sleeping partner. Therefore, a subject may not need protection from noises caused by his own breathing but may benefit from protection of breathing noises originating from a sleeping partner in the subject's sleeping environment.

As described herein, a wearable audio device or audio system detects breathing noises in a sleeping environment, distinguishes detected breathing noises of the subject from one or more sleeping partners, and outputs a masking sound in an effort to compensate for breathing noises determined to originate from the one or more sleeping partners. A "subject" may refer to a "first subject" and "sleeping partner" or "sleep partner" may both refer to a "second subject." As described herein, adjusting a masking sound refers to adjusting a sound pressure level (SPL) of a mask, adjusting a spectral composition of a mask, adjusting a level of active noise reduction (ANR), adjusting a bandwidth of ANR, or any combination thereof. Intelligently masking the breathing noises of the one or more sleeping partners while not attempting to cover up breathing noises of the subject protects the subject's sleep while simultaneously decreasing the subject's exposure to unnecessary masking sounds.

FIG. 1 illustrates example components of an audio device, in accordance with certain aspects of the present disclosure. In an example, the audio device is a headphone that fits around, on, or in an ear and that radiates acoustic energy into the ear canal. Headphones may be referred to as earphones, earpieces, headsets, earbuds, or sport headphones, and can be wired or wireless. In another embodiment, the audio device is another wearable device, such as a sleep mask or a device to be worn on a wrist. In an action, the audio device 100 is configured to perform ANR. Any or all of the components in FIG. 1 may be combined into multi-function components.

In one example, the audio device 100 includes a microphone 102, a biosensor 104, a memory and processor 106, communication unit 108, transceiver 110, and audio output transducer or speaker 112.

The microphone 102 is configured to detect the ambient noise. For example, the microphone is configured to detect breathing noises in a sleep environment of the wearable device 100. In aspects, the microphone is used to detect directionality of detected breathing noises. The microphone is configured to convert the detected noise into electrical signals.

The biosensor 104 is configured to sense or calculate a biosignal parameter of a subject wearing the audio device 100. According to an example, the biosensor 104 is one of a photoplethysmography (PPG) sensor, electroencephalogram (EEG) sensor, electrocardiogram (ECG) sensor, electrooculogram (EOG) sensor, electromyogram (EMG) sensor, accelerometer, a microphone, a device configured to detect vibrations occurring in a subject's throat, or other suitable devices. The biosensor 104 may be any sensor configured to determine, sense, or calculate a subject's biosignal parameter. In one example, the biosensor 104 is located on an ear tip of at least one earpiece, thereby contacting the subject's skin when inserted in the subject's ear.

In an example, the biosensor 104 is configured to determine the subject's pattern of inhaling. Audible breathing noises such as snoring are associated with sounds occurring during inhalation as opposed to exhalation. By correlating detected breathing noises with the subject's pattern of inhalation, the audio device is configured to determine what, if any, portion of the detected breathing noises in the subject's sleeping environment are attributable to the subject himself. In an example, the biosensor 104 is configured to determine the subject's pattern of exhaling. In some instances or for some people or subject, audible breathing noises such as snoring may be associated with sounds occurring during exhalation as opposed to inhalation. By correlating detected breathing noises with the subject's pattern of exhalation, the audio device is configured to determine what, if any, portion of the detected breathing noises in the subject's sleeping environment are attributable to the subject himself.

In an example, the biosensor is configured to collect information indicative of the subject's sleep condition. A subject's likelihood of sleep disruption when exposed to same noise is dependent of the subject's sleep condition. When the subject's sleep condition is more vulnerable, exposure to a noise may have a high probability of disturbing the subject. The subject's sleep is less likely to be disrupted when the subject is exposed to the same noise while in a less vulnerable sleep condition. One or more of a heart rate, heart rate variability, respiration rate, EEG, EOG, EMG, motion of the subject, or other suitable parameters are used to determine the vulnerability of the subject's sleep.

A SPL of the mask may increase, the frequency spectrum of the mask may be adjusted, the ANR bandwidth, or ANR level may change in an attempt to cover up the perception of a sleeping partner's breathing noises based on the subject's sleep vulnerability. In an example, a mask level may decrease, the frequency spectrum of the mask may change, the ANR bandwidth may decrease, or the ANR level may decrease to compensate for audible breathing noises of a sleeping partner when the subject's sleep is determined to be less vulnerable. In aspects, the mask level increases, the frequency spectrum of the mask may change, or the ANR bandwidth and level increases when the subject's sleep is determined to be more vulnerable. In aspects, depending on the spectral composition of the breathing noises, a spectral composition of the mask may vary in an effort to create a broad sound that does not peak in any single pitch or group of sounds. As an example, if a snore included a high pitched whistle, than the spectral composition of the sound may adjust around that frequency to merge the snoring sound into the masking sound, thus creating the illusion of the snoring sound being absent.

The memory and processor 106 control the operations of the audio device 100. The memory stores program code for controlling the memory and processor 106. The memory may include Read Only Memory (ROM), a Random Access Memory (RAM), and/or a flash ROM.

The processor 106 controls the general operation of the audio device 100. The processor 106 performs process and control for audio and/or data communication. In addition to the general operation, the processor 106 is configured to determine the breathing noises originating from a sleep partner as compared to breathing noises originating from the subject wearing the audio device. In an example, the processor 106 is configured to compare detected audible breathing noises to a breathing architecture of the subject wearing the audio device 100 to determine if the detected breathing noises originated from the subject or the sleeping partner. In an aspect, the processor 106 is configured to determine a time-frequency pattern of the breathing noises originating from the sleeping partner. In an aspect, the processor 106 is configured to determine a time-frequency pattern of the breathing noises originating from the subject. As described herein, the audio device masks detected breathing noises determined to originate from one or more sleeping partners.

In an aspect, the processor 106 is configured to determine that a portion of the detected breathing noises originated from the first subject. As described herein, the audio device is further configured to intelligently refrain from masking detected breathing noises determined to have originated from the subject wearing the audio device 100.

In an aspect, the processor compares the detected breathing noises, a breathing architecture of the subject wearing the audio device 100, and the sleep condition of the subject wearing the audio device. As described in more detail below, the breathing architecture may be detected by a microphone or biosensor, either on the audio device or external to the audio device, and the subject's sleep condition may be determined based on signals obtained from the biosensor. The breathing architecture may further be based on user input, such as the subject selecting whether or not the subject is alone in the sleeping environment.

According to aspects, the processor intelligently predicts if the detected breathing noises will disturb the subject's sleep based on the subject's sleep condition. In aspects, the audio device determines the subject's sleep is vulnerable. In response to vulnerable sleep, the audio device masks breathing sounds originating from a sleeping partner, increases the level of the mask output, alters a frequency spectrum of the mask, increases the ANR level, or adjusts the ANR bandwidth. In aspects, the audio device later determines the subject is in a deeper, less vulnerable sleep condition. In response to determining less fragile sleep, the audio device may stop masking, mask a reduced level, alter a frequency spectrum, reduce the ANR level, or adjust the ANR bandwidth to mask a sleeping partner's breathing noises.

According to aspects, the processor is configured to determine a pattern of any predicted, disturbing breathing sounds from a sleeping partner. The audio device monitors audible breathing noises for a period of time in an effort to determine a time-frequency pattern of the breathing noises of a sleeping partner. The masking is aligned with the pattern of predicted disturbing sounds. In an example, aligning the mask means varying a sound level of the masking sounds such that the mask matches the pattern of breathing noises, altering the frequency spectrum of the mask to effectively match the pattern of breathing noises, varying the ANR level to compensate for the pattern of breathing noises, or adjusting the ANR bandwidth to match the pattern of breathing noises. Aligning the masking with the pattern of disturbing noises allows the audio device to protect sleep and minimize the subject's exposure to unnecessary masking sounds.

The communication unit 108 facilitates a wireless connection with one or more other devices. For example, the communication unit 108 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols.

In an example, the communication unit 108 wirelessly communicates with a handheld device such as a tablet or cell phone. In one example, a subject wearing the audio device 100 inputs information about his sleeping environment in an application on a handheld device. Examples of information include if the subject identifies as a snorer or if the subject has a sleeping partner.

According to aspects, if the subject does not identify as snoring while asleep, the audio device may mask all detected breathing noises without attempting to determine a source of detected breathing noises. A subject who identifies as a non-snorer may be unaware that he actually snores or generates audible breathing noses detectable by the audio device. Therefore, even if the subject identifies as a non-snorer, according to aspects, the audio device may monitor for breathing noises and compare the breathing noises to a breathing architecture of the subject to identify a portion of the breathing noises predicted to disrupt the subject's sleep. The audio device may further monitor for breathing noises and compare the breathing noises to a detected direction of snoring sounds or a source of vibrations in the subjects to identify a portion of the breathing noises predicted to disrupt the subject's sleep.

In aspects, the subject may record actual breathing noises of a sleeping partner. This historical sound clip is compared to detected noises observed by the audio device to identify with increased confidence, breathing noises of a sleeping partner. In aspects, the subject may record the subject's own breathing noises. This historical information is compared to detected noises observed by the audio device. In aspects, the audio device may correlate portions of the detected noise with historical recorded breathing sounds of the subject. The audio device may determine with increased confidence that the correlated portion of the detected noise originated from the subject and therefore should not be masked. In aspects, the audio device may use pre-recorded sound clips of the subject's breathing sounds, the sleeping partner's breathing sounds, or both the subject and the sleeping partner's breathing sounds to identify portions of detected noise that are associated with each of the subject and the sleeping partner.

The transceiver 110 transmits and receives information via one or more antennae to exchange information with one or more other devices. The transceiver 110 is not necessarily a distinct component. The transceiver 110 is configured to transmit and receive information from an application running on an external wireless device, such as a handheld device. According to aspects, the transceiver 110 in combination with the communication unit 108 communicates with the internet, networks, or hub services such as the cloud.

The audio output transducer 112 may be also known as a driver or speaker. In some examples, more than one output transducer is used. The transducer converts electrical signals into sound and converts sound into electrical signals. The transducer is configured to output a masking sound to compensate for breathing noises determined to originate from a sleeping partner as opposed to breathing noises that may have originated from the wearer of the audio device 100.

FIG. 1 illustrates communication between certain modules of an example open audio device; however, aspects of the disclosure are not limited to the specific illustrated example. According to aspects, any module 102-112 is configured to communicate with any other module in the audio device. In one example, all modules are connected to and communicate with each other.

According to aspects, the audio device 100 includes fewer components than illustrated in FIG. 1. For example, the audio device may not include a biosensor or a microphone. Even without certain components, the audio device is configured to intelligently mask breathing sounds. For example, microphones placed in the subject's sleeping environment detect breathing noises and communicate the detected noises and time-frequency pattern of the noises to the audio device. The microphones placed in the subject's sleeping environment may further detect a directionality of the detected breathing noises. In another example, an occupancy sensor or motion sensor placed under the subject's mattress is used to determine the presence or absence of a sleeping partner. When a sleeping partner is not present, the audio device refrains from masking detected breathing sounds. When a sleeping partner is detected, the audio device performs the intelligent masking described herein. In aspects, the audio device may not have a biosensor. The biosignal parameter of the subject may be determined using a contactless sensor. The biosignal parameter is communicated to the audio device in an effort to determine the likelihood of a sleeping partner's breathing noises disrupting the subject's sleep.

Figure 2:
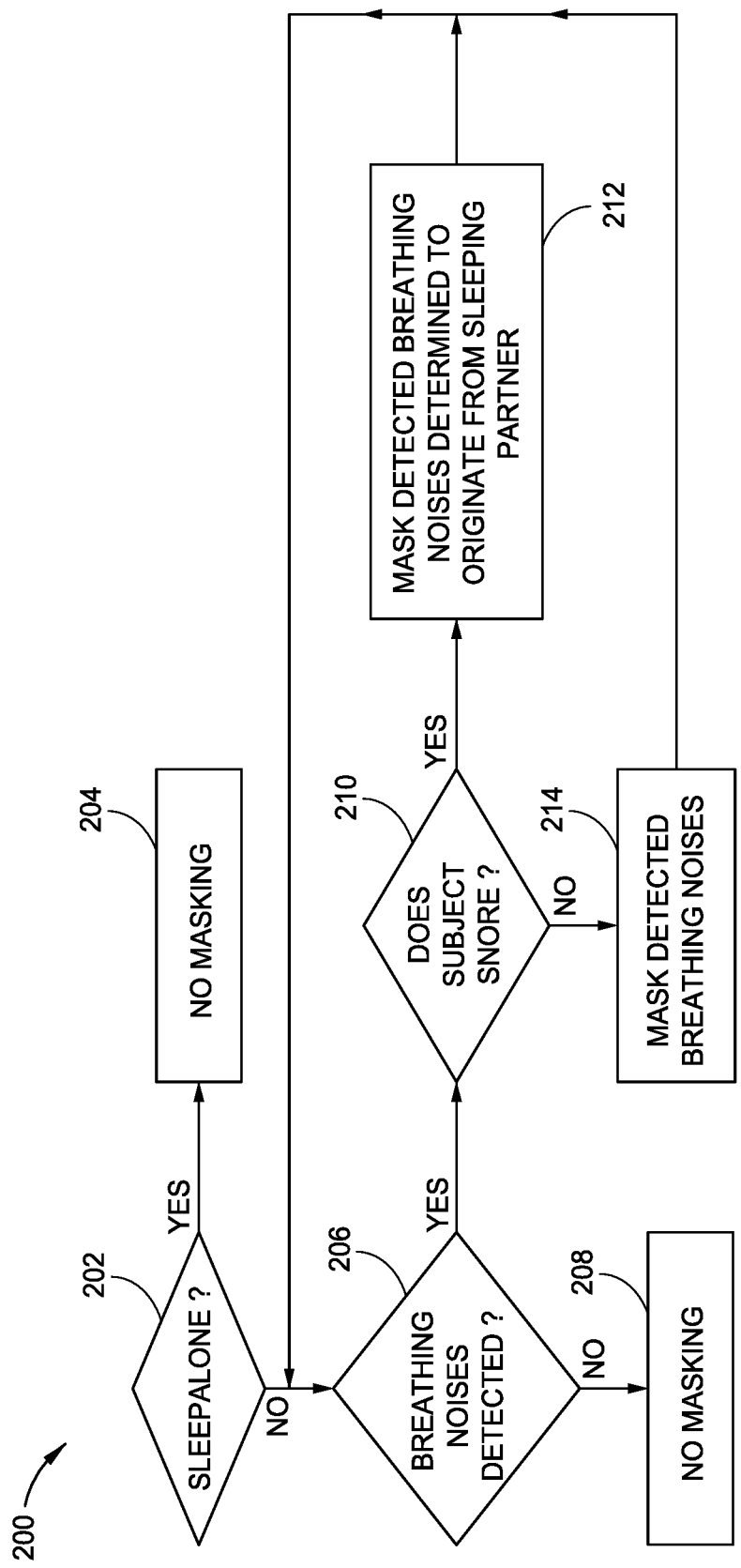
FIG. 2 illustrates an example method for dynamically masking audible breathing noises.

FIG. 2 illustrates example operations 200 for masking breathing noises determined to originate from a sleep partner and therefore determined to disturb the subject's sleep. The operations 200 may be performed by the audio device 100. In one example, the audio device 100 that performs the operations 200 does not include a biosensor.

At 202, the audio device determines if the subject is sleeping alone. In an example, the subject manually inputs the presence or absence of a sleep partner. The subject may input this information using an application executed on the audio device or a handheld device in communication with the audio device 100.

In an aspect, an occupancy sensor detects the presence of one subject or more than one subject. Examples of occupancy sensors include a motion-sensing pad placed underneath a mattress of a bed, a passive infrared sensor, a thermal sensor, a movement sensor, a pressure sensor, an acoustic sensor, an image recognition device, or other suitable devices.

Masking detected breathing noises may be unnecessary if the subject is determined to be sleeping alone. Therefore, to reduce the subject's exposure to excessive noise, at 204, the audio device refrains from outputting masking sounds.

If the subject is determined to have a sleeping partner, at 206, the audio device determines if breathing noises are detected in the subject's sleeping environment. In an example, the audio device is configured with patterns of inhaling breathing sounds generally associated with snoring. In an example, the subject uploads a recorded audio clip of observed snoring by a sleeping partner in the sleeping environment.

When breathing noises are detected, at 210, the audio device determines if the subject snores. In one example, such as when the audio device does not include a biosensor, the subject may input whether he self-identifies as a snorer. If the subject does not identify as a snorer and the subject is determined to have a sleeping partner, the audio device, at 214, masks detected breathing noises.

Returning to 210, in an example, a sensor detects vibration from the nose or throat of the subject that indicates snoring. The sensor transmits this information to the audio device. The sensor may be any type of sensor configured to detect a subject's breathing rate. In an example, a microphone (either internal or external to the audio device) detects snoring sounds originating from the subject. According to aspects, a wide-band accelerometer disposed on an in-ear audio device or a radio frequency sensor detects the subject's breathing. The detected breathing patterns are compared to detected breathing sounds to determine if the breathing noises are attributable to the subject.

If the subject is determined to snore, at 212, the audio device masks detected breathing noises determined to originate from a sleeping partner. In aspects, the audio device determines the portion of detected breathing noises that originated from the subject. The portion of noises determined to originate from the user are removed from the detected signal. The audio device masks the remaining portion of noises, as they are believed to have originated from a sleeping partner.

In one example, the audio device correlates the detected breathing noises with the detected vibrations of the subject. Breathing noises that time-align with the subject's detected vibrations are assumed to originate from the subject. Breathing noises that do not align with the subject's detected vibrations are assumed to originate from a sleeping partner. The audio device refrains from masking any breathing noises determined to originate from the subject and masks only the breathing noises determined to originate from another subject, such as the sleeping partner.

Optionally, at 212, the audio device determines the sleep condition of the subject. The sleep condition is determined using a biosensor. Based on a collected biosignal parameter, the audio device determines the user's sleep fragility. In an example, the subject's biosignal parameter, or values of a biosignal parameter over a period of time, is compared to benchmark biosignal parameters to determine the subject's sleep fragility. Benchmarks may be associated with collected parameters from subset of the population. Benchmark data may include information from published studies, samples obtained from groups of people, internal field testing, etc. In aspects, the benchmarks are specific to a gender, age range, or combination of gender and age range. Based on the subject's gender and age, the audio device compares the subject's collected biosignal parameters with the benchmark data to determine sleep vulnerability. When the subject's sleep is more vulnerable, the audio device alters the spectral content of the mask, increases a sound pressure level of the mask, or increases the ANR bandwidth or ANR sound pressure level to cover-up the sleeping partner's breathing noises. When the subject's sleep is determined to be less fragile, the spectral content of the mask is adjusted, the sound pressure level of the mask is decreased, the ANR bandwidth is decreased, or the ANR sound pressure level is decreased. According to aspects, the audio device may determine if adjusting the mask affect the subject's sleep in response to a particular sound. A learning algorithm may be used to adjust how the mask is adjusted in the future in response to similar sounds.

When the subject is determined not to sleep alone and when breathing noises are not detected in the subject's sleep environment, at 208, the audio device refrains from outputting a masking sound. In one embodiment, the masking sound is refrained from increasing in volume, but may continue to be output at a lower volume or level when breathing noises are not detected in the subject's sleeping environment.

When the subject is determined not to sleep alone, when breathing noises are detected in the subject's sleep environment, and when the subject is determined not to snore, at 214, the audio device masks the detected breathing noises. Optionally, the masking is based on a determined sleep condition of the subject. As described with reference 212, the audio device may output sound masking at a higher sound pressure level when the subject's sleep condition is determined to be more vulnerable as compared to when the subject is in a deep sleep and less susceptible to waking up.

Figure 3:
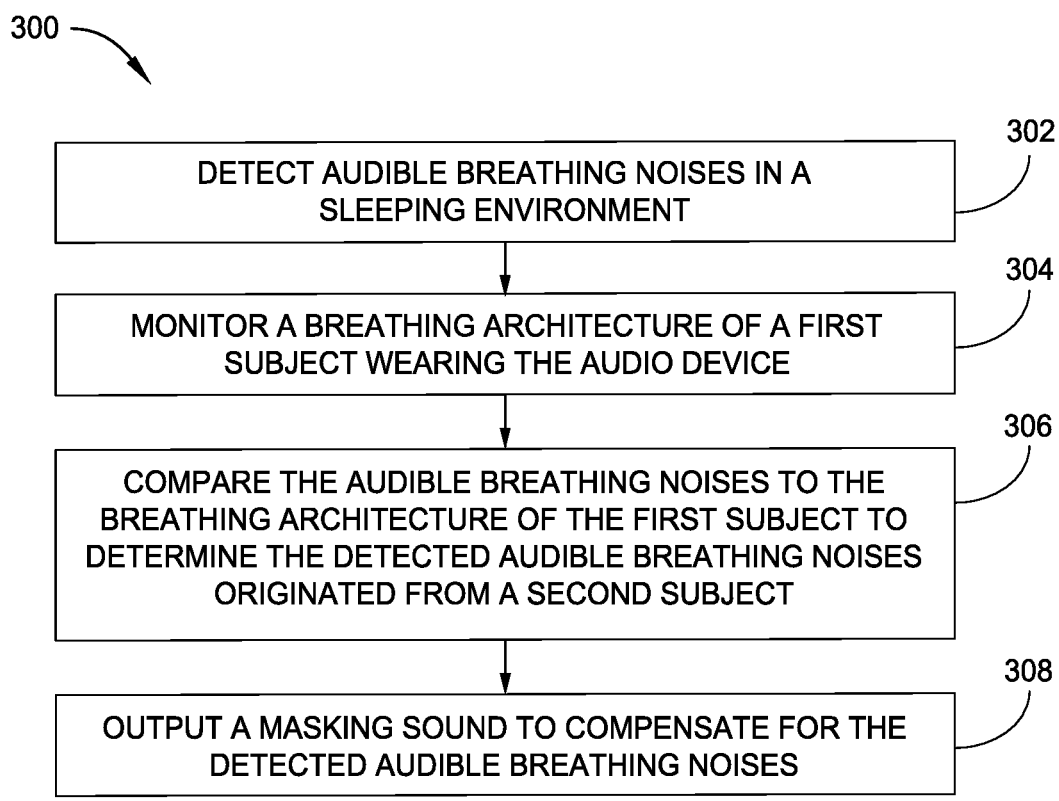
FIG. 3 illustrates an example method for dynamically masking audible breathing noises.

FIG. 3 illustrates example operations 300 for dynamically masking breathing noises determined to originate from a sleeping partner. The operations 300 may be performed by the audio device 100. The audio device 100 may not have all of the components illustrated in FIG. 1.

At 302, using a microphone, the audio device detects audible breathing noises in a sleeping environment of the subject.

At 304, using at least one biosensor, the audio device monitors a breathing architecture of a subject wearing the audio device. Breathing architecture refers to the timing of inhalation and exhalation of the subject.

At 306, a processing unit in the audio device is configured to compare the audible breathing noises to the breathing architecture of the subject to determine if the detected audible breathing noises originated from a sleeping partner.

At 308, at least one speaker in the audio device is configured to output a masking sound to compensate for the detected audible breathing noises determined to originate from the second subject.

In aspects, the processing unit is further configured to compare the breathing architecture of the subject and the detected breathing noises to determine what portion, if any, of the detected breathing noises originated from the subject. As one's own breathing sounds typically do not disrupt one's sleep, the audio device refrains from masking a portion of the breathing noises that are determined to originate from the subject.

In an example, the audio device determines a pattern of the subject's breathing architecture. The pattern is determined using, for example, a microphone, accelerometer, or biosensor. The pattern includes a time, frequency, or time-frequency pattern of inhalation (or exhalation) associated with the subject. When a time, frequency, or time-frequency of the detected breathing noises are time-aligned with the time, frequency, or time-frequency of the subject's breathing architecture, respectfully, the audio device determines the aligned portion is associated with the subject's own breathing. Therefore, the audio device may refrain from masking the subject's breathing.

FIG. 2 and FIG. 3 illustrate example operations for illustration purposes only. Aspects cover any method, device, or system capable of intelligently attempting to cover up a subject's perception of breathing noises originating from a sleeping partner. Optionally, in certain aspects, the mask is further adjusted based on the subject's sleep condition and/or information about the subject's sleeping environment. Adjusting how the perception of breathing noises originating from a sleeping partner are covered up to create a personalized user experience while reducing the subject's exposure to unnecessary and potentially harmful sounds. In an example, a system includes any combination of a wearable, smart device, bedside unit, microphones, or sensors. A bedside unit may be a stationary smart device, such as a smart speaker. The wearable, smart device, and bedside unit may include any combination of the components illustrated in the audio device of FIG. 1.

In one example, a system including a microphone, processor, wearable audio device, and bedside unit are configured to dynamically mask breathing noises determined to originate from a sleep partner. The microphone may be disposed in a sleep environment and may detect breathing noises. A biosensor on the wearable audio device monitors a breathing architecture of the sleeping subject. A processor of the audio device compares the audible breathing noises to the breathing architecture to identify a portion of the audible breathing noises predicted to disrupt the subject's sleep. The processor further determines a pattern of the breathing noises predicted to disrupt the subject's sleep. In an aspect, a masking sound is output by the wearable audio device to compensate for the portion of the audible breathing noises predicted to disrupt the subject's sleep. In an aspect, a bedside unit configured to communicate with one or more of the wireless audio device or the processor is configured to output the masking sound.

In another system, the breathing architecture of both the subject and the sleeping partner are monitored. In an example, each subject is in contact with a separate biosensor. A processor uses the collected information to determine the portion of detected noise attributable to each of the subject and the sleeping partner. Portions of the noise determined to originate from the sleeping partner are masked.

In an example, a microphone (on board or external to the audio device) detects breathing architecture and directionality of detected breathing noises and a processor determines a time, frequency, or time-frequency pattern of inhalation associated with the sleep partner of the subject. The audio device determines, based on distance or other factors, that the detected breathing architecture is associated with the sleeping partner and not the subject. When a time, frequency, or time-frequency of the detected breathing noises are time-aligned with the time, frequency, or time-frequency of the sleeping partner's breathing architecture, respectfully, the audio device determines the aligned portion is associated with the sleeping partner's breathing. Therefore, the audio device masks the portion of the breathing noises associated with the sleeping partner's breathing.

According to aspects, the audio device adjusts the masking based on at least one measured biosignal parameter of the subject. The biosignal parameter is used to estimate the sleep condition of the subject. When the subject's sleep is determined to be compromised, the audio device increases a SPL of the mask, adjusts a spectral content of the mask, increases an ANR level, adjusts the ANR bandwidth, or performs a combination thereof.

Aspects of the present disclosure provide methods, devices, and systems configured to dynamically protect a first subject's sleep by masking audible breathing noises determined to originate from one or more other subjects. According to aspects, the audio device or system described herein, is also configured to predictively mask potentially disturbing sounds prior to their occurrence as described in U.S. patent application Ser. No. 16/278,322 entitled "Dynamic Masking With Dynamic Parameters," filed on Feb. 18, 2019, which published as US 2020/0265823 A1, which is hereby incorporated by reference in its entirety.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. An audio device, comprising:
at least one microphone configured to detect audible breathing noises in a sleeping environment;
at least one biosensor configured to monitor a breathing architecture of a first subject, wherein the breathing architecture is a timing of inhalation and exhalation of the first subject as detected by the at least one biosensor;
a processing unit configured to compare the audible breathing noises to the breathing architecture of the first subject to determine the detected audible breathing noises originated from a second subject; and
at least one speaker configured to output a masking sound to compensate for the detected audible breathing noises.

2. The audio device of claim 1, wherein:
the processing unit is further configured to determine, based on the comparison of the audible breathing noises to the breathing architecture of the first subject, that a portion of the audible breathing noises originated from the first subject, and
the at least one speaker is configured to refrain from outputting the masking sound to compensate for the portion of the audible breathing noises determined to originate from the first subject.

3. The audio device of claim 1, wherein:
the processing unit is further configured to determine a time-frequency pattern of the audible breathing noises originating from the second subject, and
the masking sound is aligned with the determined time-frequency pattern.

4. The audio device of claim 1, wherein the at least one biosensor is configured to measure at least one biosignal parameter indicative of a sleep condition of the first subject, wherein the at least one biosignal parameter comprises at least one of a heart rate, a heart rate variability, a respiration rate, an electroencephalogram (EEG), an electrooculogram (EOG), an electromyogram (EMG), or a motion of the first subject.

5. The audio device of claim 4, wherein the processing unit is further configured to adjust the masking sound based on the detected audible breathing noises and the at least one measured biosignal parameter, and wherein adjusting the masking sound comprises adjusting at least one of: a spectral content of the masking sound, a sound pressure level of the masking sound, or an active noise reduction (ANR) level.

6. The audio device of claim 1, wherein the at least one biosensor is configured to monitor the breathing architecture of the first subject by measuring at least one of: a breathing pattern of the first subject or vibrations of the first subject.

7. A method for protecting a sleep pattern of a first subject performed by at least one processor coupled to a memory, a speaker and at least one biosensor, the memory including instructions executable by the at least one processor to:
  detect audible breathing noises in a sleeping environment;
  monitor a breathing architecture of the first subject while the first subject is sleeping in the sleeping environment, wherein the breathing architecture is a timing of inhalation and exhalation of the first subject as detected by the at least one biosensor;
  compare the audible breathing noises to the breathing architecture of the first subject to identify a portion of the audible breathing noises predicted to disrupt the first subject's sleep;
  determine a pattern of the portion of the audible breathing noises predicted to disrupt the first subject's sleep; and
  output, by the speaker, a masking sound to compensate for the portion of the audible breathing noises predicted to disrupt the first subject's sleep, wherein the masking sound is time aligned with the pattern.

8. The method of claim 7, wherein the memory further includes instructions executable by the at least one processor to receive, from the first subject, at least one of: one or more characteristics of the sleeping environment or one or more characteristics of the breathing architecture of the first subject prior to the comparing.

9. The method of claim 7, wherein the memory further includes instructions executable by the at least one processor to measure at least one biosignal parameter of the first subject, wherein one or more values of the biosignal parameter are indicative of a sleep condition of the first subject prior to the comparing, wherein the at least one biosignal parameter comprises at least one of a heart rate, a heart rate variability, a respiration rate, an electroencephalogram (EEG), an electrooculogram (EOG), an electromyogram (EMG), or a motion of the first subject.

10. The method of claim 9, wherein in order to compare the audible breathing noises to the breathing architecture of the first subject, the memory further includes instructions executable by the at least one processor to compare the audible breathing noises, the breathing architecture of the first subject, and the sleep condition of the first subject to identify the portion of the audible breathing noises predicted to disrupt the first subject's sleep.

11. The method of claim 10, wherein the memory further includes instructions executable by the at least one processor to adjust the masking sound prior to outputting the masking sound based on the sleep condition of the first subject and the portion of the audible breathing noises predicted to disrupt the first subject's sleep, wherein adjusting the masking sound comprises adjusting at least one of: a spectral content of the masking sound, a sound pressure level of the masking sound, or an active noise reduction (ANR) level.

12. The method of claim 7, wherein:
  in order to compare the audible breathing noises to the breathing architecture of the first subject, the memory further includes instructions executable by the at least one processor to identify a second portion of the audible breathing noises that are not predicted to disrupt the first subject's sleep, and the memory further includes instructions executable by the at least one processor to refrain from outputting a masking sound for the identified second portion of the audible breathing noises.

13. An audio system, comprising:
  at least one microphone for detecting audible breathing noises in a sleeping environment;
  at least one biosensor for:
    monitoring a breathing architecture of a first subject, wherein the breathing architecture is a timing of inhalation and exhalation of the first subject as detected by the at least one biosensor, and
    measuring at least one biosignal parameter of the first subject, wherein one or more values of the biosignal parameter are indicative of a sleep condition of the first subject;
  a processing unit configured to:
    compare the audible breathing noises, the breathing architecture of the first subject, and the sleep condition of the first subject;
    predict whether the audible breathing noises will disturb the first subject's sleep based on the comparison to identify predicted disturbing noises; and
    determine a pattern of the predicted disturbing noises; and
  at least one speaker for outputting a masking sound to compensate for the predicted disturbing noises, wherein the masking sound is time aligned with the pattern of the predicted disturbing noises.

14. The audio system of claim 13, wherein the processing unit is further configured to determine a second subject is in the sleeping environment.

15. The audio system of claim 14, wherein the audio system comprises:
  an occupancy sensor configured to determine presence of the second subject in the sleeping environment.

16. The audio system of claim 14, wherein the processing unit is further configured to receive input from the first subject regarding characteristics of breathing architecture of the first subject and how many subjects are in the sleeping environment.

17. The audio system of claim 13, wherein a first device comprises the at least one biosensor, and wherein the first device is a wearable device.

18. The audio system of claim 17, wherein the first device further comprises the at least one speaker.

19. The audio system of claim 13, wherein a second device comprises the at least one microphone, and wherein the second device is a bedside unit.

20. The audio system of claim 19, wherein the second device further comprises the at least one speaker.

* * * * *